(12) United States Patent
Whelan

(10) Patent No.: US 9,532,926 B2
(45) Date of Patent: Jan. 3, 2017

(54) SAMPLING PORT

(71) Applicant: Chris Whelan, Annandale (AU)

(72) Inventor: Chris Whelan, Annandale (AU)

(73) Assignee: NOBLE HOUSE GROUP PTY. LTD. (AU)

(*) Notice: Subject to any disclaimer, the term of this patent is extended or adjusted under 35 U.S.C. 154(b) by 0 days.

(21) Appl. No.: 14/404,645

(22) PCT Filed: May 31, 2013

(86) PCT No.: PCT/AU2013/000572
§ 371 (c)(1),
(2) Date: Dec. 1, 2014

(87) PCT Pub. No.: WO2013/177628
PCT Pub. Date: Dec. 5, 2013

(65) Prior Publication Data
US 2015/0144224 A1 May 28, 2015

(30) Foreign Application Priority Data
May 31, 2012 (AU) ................................ 2012902269

(51) Int. Cl.
A61J 1/20 (2006.01)
B65B 3/00 (2006.01)
G01N 1/10 (2006.01)

(52) U.S. Cl.
CPC ................. *A61J 1/2089* (2013.01); *A61J 1/20* (2013.01); *A61J 1/2096* (2013.01); *B65B 3/003* (2013.01);
(Continued)

(58) Field of Classification Search
CPC ............ A61J 1/20; A61J 1/2006; A61J 1/201; A61J 1/2048; A61J 1/2065; A61J 1/2058; A61J 1/2096; A61J 1/2055; B65B 3/003
(Continued)

(56) References Cited

U.S. PATENT DOCUMENTS 5,211,623 A * 5/1993 Sarkozi ................... A61F 5/055
128/DIG. 23
5,647,845 A * 7/1997 Haber ....................... A61J 1/10
604/32

(Continued)

FOREIGN PATENT DOCUMENTS

EP 2332510 B1 6/2011
WO WO 2009/105489 A1 8/2009

*Primary Examiner* — Timothy L Maust
*Assistant Examiner* — Timothy P Kelly
(74) *Attorney, Agent, or Firm* — Galbreath Law Offices, P.C.; John A. Galbreath

(57) ABSTRACT

A sampling port (10) has a body (12) having an space (35) open at one end (20) and adapted to receive a sampling vial (70) with an cannula (24) extending longitudinally along the space (35) with a pointed end (26) facing the open end (20), whereby a sampling vial passed into the space from the open end may be impaled on the cannula. The port includes at least one guide member (36) extending into the space (35) to reduce the effective size of part of the space (35), the at least one guide member (36) guiding a vial (50) of a first size when inserted into the open end (20) and the at least one guide member (36) being movable to allow a vial (70) of a size larger than the first size to be inserted into the space.

17 Claims, 11 Drawing Sheets

(52) U.S. Cl.
CPC .................. *G01N 1/10* (2013.01); *A61J 1/201* (2015.05); *A61J 1/2055* (2015.05); *A61J 1/2065* (2015.05)

(58) Field of Classification Search
USPC .................. 141/329–330, 383; 604/411, 414
See application file for complete search history.

(56) References Cited

U.S. PATENT DOCUMENTS

| | | | |
|---|---|---|---|
| 2002/0127150 A1* | 9/2002 | Sasso | A61J 1/2096 422/569 |
| 2003/0153895 A1 | 8/2003 | Leinsing | |
| 2010/0179506 A1* | 7/2010 | Shemesh | A61J 1/2096 604/414 |
| 2013/0066293 A1* | 3/2013 | Garfield | A61J 1/10 604/408 |

* cited by examiner

SAMPLING PORT

FIELD OF INVENTION

This invention relates to medical sampling ports and more particularly providing a sampling port that can accommodate different diameter sampling bottles and/or vials. For ease of reading the term "sampling vial" alone is used in this specification and the term "sampling vial" is to be interpreted to include both sampling vial and sampling bottle.

BACKGROUND

Medical sampling ports are devices that allow a sample of fluid to be withdrawn, typically into a sampling vial. Typical sampling ports are tubular with one end closed to form a base and the other end open. A cannula is centrally mounted on the base and extends within the port toward the open end. The end of the cannula ends short of the end of the sampling port and so is not exposed. A sampling vial may be passed into the open end and impaled on the cannula.

It is desirable that the sampling vial when inserted into the sampling port is prevented from significant sideways movement, as this may result in damage to the cannula or incomplete penetration of the cannula into the sampling vial.

Sampling vials generally come with portions to be inserted in to a sampling port in two different maximum diameters. It is desirable that these different diameters are readily accommodated by the sampling port without the need for separate guides or the like that are inserted or removed from the sampling port to accommodate the different diameters.

SUMMARY OF THE INVENTION

In one broad form the invention provides a sampling port having:
- a body having a space having a longitudinal direction, open at one end and adapted to receive a sampling vial;
- an cannula having an axis and extending longitudinally along the space with a pointed end facing the open end, whereby a sampling vial passed into the space from the open end may be impaled on the cannula;
- at least one guide member extending into the space to reduce the effective size of part of the space;
- the at least one guide member guiding a vial of a first size when inserted into the open end;
- the at least one guide member movable to allow a vial of a size larger than the first size to be inserted into the space and guided by the at least one guide member onto the cannula.

Movement of the guide member is preferably caused by the vial as it is inserted into the sampling port. However, the invention includes movement by other ways.

At least one guide member may be mounted for movement about a hinge. However, movement may be by one or more of bending or deflection other than rotation about a hinge, or by movement of the guide member as a whole. In a preferred form the at least one guide member bends around a vial.

The space may have a first portion of a first size. The space may have a second portion of a second, smaller size.

At least part of the space may be defined by at least one first wall portion.

At least part of the space may be defined by at least one second wall portion.

At least one guide member may be mounted on at least one wall.

At least one guide member may extend from at least one wall portion.

At least one guide member may be formed with the at least one wall portion.

At least one guide member may be at least partially defined by two spaced apart slots in at least one wall portion.

At least part of at least one guide member may be located nearer the axis of the cannula than an adjacent wall portion.

At least part of at least one guide member may be movable to be located equidistant with an adjacent wall portion from the axis of the cannula or further from the axis of the cannula than an adjacent wall portion.

At least one first wall portion may define a space portion of a size adapted to receive a vial larger than the first size.

At least one second wall portion may define a space portion of a size adapted to receive a vial of the first size.

The space may be defined by a generally tubular wall. In the first position at least part of the at least one guide member may be located inwards relative to the majority of the wall of the first portion.

The second space portion may be sized so that the wall of the second space portion acts as a guide for vials having the first size.

The first space portion may be sized so that the wall of the first space portion acts as a guide for vials having the second size.

The space may have a third space portion at the open end which is of a larger size than the first space portion. This third space portion may be defined by the surface of an annular flange that extends radially outwards toward the open end. The at least one guide member may extend into the third space portion.

At least one guide member may have a first portion that extends transversely within the space. The first portion may extend both transversely and longitudinally within the space.

At least one guide member may have a second portion that extends longitudinally along the space. The second portion may depend from the first portion, when the first portion is present.

At least one guide member may extend from or adjacent the open end of the sampling port.

At least one guide member may be located within the third space portion.

At least part of the space may be defined by at least one first surface.

At least one first surface may act as a guide for vials having a size larger than the first size.

At least part of at least one guide member may comprise at least one first surface.

At least part of the space may be defined by at least one second surface.

The at least one second surface may act as a guide for vials having the first size.

At least part of at least one guide member may comprise at least one second surface defining at least part of a second space portion.

The sampling port may include a centring surface at or adjacent the open end adapted to centre a vial over the cannula.

The sampling port may include at least two guide members that cooperate with each other to limit outwards radial movement of at least part of the at least two guide members.

The sampling port may include at least two guide members connected to each so as to limit outwards radial movement of at least part of the at least two guide members.

The sampling port may include at least two guide members connected to each so as to limit outwards radial movement of at least part the at least two guide members and each further including a guide portion and at least one joining portion, said at least one joining portion extending from the guide portion and each at least one joining portion joined or connected to a joining portion of at least one other of said at least two guide members.

At least part of at least one guide member may bend around a vial.

The sampling port may include three guide members spaced substantially equally about the axis of the cannula.

The sampling port may include at least one guide member recess adapted to receive at least part of a guide member.

At least one guide member recess may be defined by at least one surface.

At least one guide member recess may be defined by the body.

A guide member may be a part of the tubular wall and extend toward the axis of the cannula more than the remainder of the wall. However, at least one guide member may be a separate component.

A guide member may be formed as part of the wall and defined by two spaced apart slots either side of the or each guide member. A recess may be provided to receive at least part of a guide member.

The at least one guide member may extend into both the first and second space portions.

In one form the sampling port has a second space portion defined by a wall and the at least one guide member is an extension of the wall of the second space portion that extends into the first space portion.

When formed as part of the wall defining the space the at least one guide member may be connected to the wall at one or both ends. A connection to the wall may be in the first space portion or may be outside the first space portion.

Where there is a second space portion at least one guide member may extend from the second space portion into the first space portion. Where there is a third space portion at least one guide member may extend from the third space portion into the first space portion.

At least one guide member may be located only within the first space portion. At least one guide member may be connected to or be part of the wall. At least one guide member may be connected to or be part of the wall of the first space portion at one or both ends within the first space portion.

The at least one guide member may comprise three guide members spaced substantially equally about the axis of the cannula.

The wall may define a generally cylindrical portion or portions having at least one recess which may receive at least one guide member.

The sampling port may include at least one protective member that in a protective position closes the open end sufficiently to substantially prevent accidental access to the cannula by a user.

The sampling port may include at least two guide members and at least one protective member located between adjacent guide members.

The sampling port may include three guide members spaced equally about the axis of the cannula and three protective members, also spaced equally about the axis of the cannula.

The at least one protective member is preferably movable from the protective position to a retracted position by movement of a vial into the space.

Movement of at least one protective includes one or more of bending, deflection, rotation about a hinge area and by movement of the at least one protective as a whole.

The sampling port may include at least one protective member recess adapted to receive at least part of a protective member.

At least one protective member recess may be defined by the body.

The wall may define a generally cylindrical portion or portions having at least one recess which may receive at least one protective member.

At least one guide member may be a protective member. At least one protective member may be a guide member.

In a preferred form of the invention there are three guide members spaced equally about the axis of the cannula and there are three protective members, also spaced equally about the axis of the cannula. The protective members are preferably positioned so that in the retracted position a protective member is located between adjacent guide members.

DETAILED DESCRIPTION OF IMPLEMENTATIONS OF THE INVENTION

Figure 3:
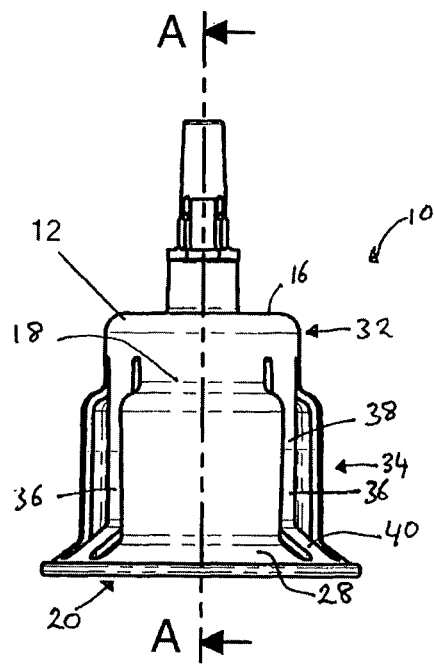
FIG. 3 is a side view of the device of FIG. 1.
Figure 4:
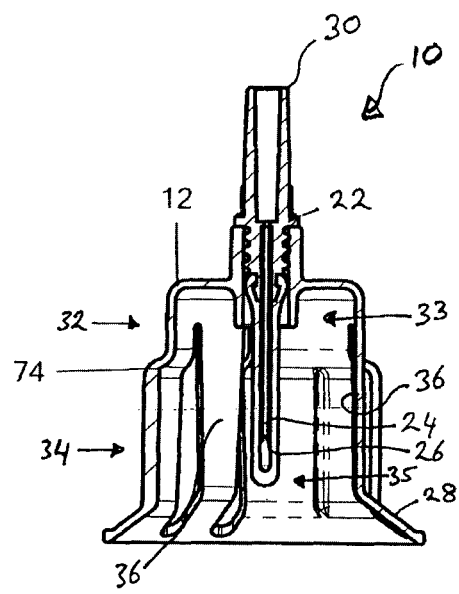
FIG. 4 is a cross sectional side view of the sampling port of FIG. 1 taken along line AA in FIG. 3.

Referring to FIGS. 1 to 7 there is shown a sampling port 10 according to one implementation of the invention.

The sampling port 10 has a generally tubular body 12. The body 12 has a base 16 at one end and a tubular side wall 18 that extends away from the base 16. The tubular side wall 18 defines an open end 20 and a space 21. Mounted on the base 16 is a needle assembly 22 having a cannula 24. The cannula 24 is mounted generally centrally and extends along the body toward the open end 20. The free end 26 of the cannula 24 is located away from the open end 20. A rubber sheath 25 surrounds the cannula 24. The open end 20 of the side wall 18 has a conical flange 28 that aids in holding the sampling port in use. The flange 28 is not essential and may be of other shapes or configurations or may be omitted.

The interior of the cannula 24 communicates with a connector or piercing device of needle assembly 22 so that fluid may pass from the connector to the cannula 24 or vice versa. In the implementation shown the connector is a male luer connector 30 and the assembly 22 is a screw fit into base 16. If desired the base 16 and assembly 22 may be formed together with the cannula mounted in the integral base. The type of connector or piercing device is not critical and variations may be used, including a male or female luer, locking luer, multi-sample (double-ended) needle, blunt cannula, spike etc.

The tubular side wall 18 is generally cylindrical and has second wall portion 32 of one diameter near the base 16 and a first wall portion 34 of a larger diameter further away from the base 16. The first wall portion 34 defines a first space portion 35 and the second wall portion 32 defines a second space portion 33. The surface of the flange 28 defines a third space portion 39.

Figure 5:
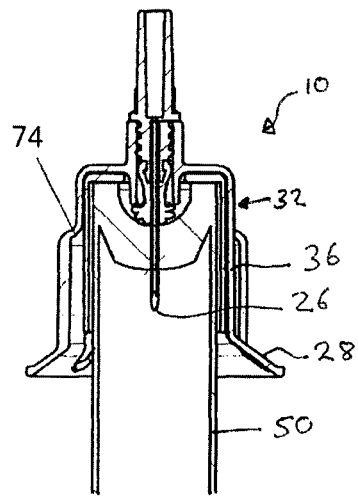
FIG. 5 is a cross sectional side view of the sampling port of FIG. 1 in use with a first size vial.
Figure 6:
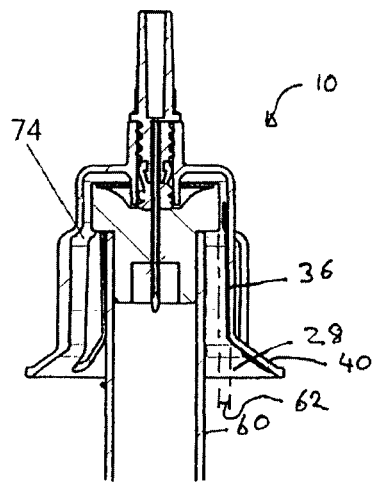
FIG. 6 is a cross sectional side view of the sampling port of FIG. 1 in use with a second size vial.

The second space portion 33 is sized to accommodate and guide a small diameter sampling vial 50, as shown in FIGS. 5 and 6.

The end 26 of the cannula extends into the larger first space portion 35 and so a small diameter vial would not be located and prevented from sideways movement by the first wall portion 34.

Three guide members 36 extend inwards from the larger diameter and define a smaller opening corresponding to the size of the smaller space portion 33 into which a small diameter vial may be inserted. In this implementation the guide members 36 are formed as part of first wall portion 34.

The guide members 36 thus partially block the larger first space portion 35 and so need to be movable outwards to allow a large diameter vial to be inserted into the large first space portion 35. In this implementation the guide members 36 are longitudinally extending. The guide members 36 extend in a slot 37 from the second wall portion 32 to the flange 28. The guide members 36 are preferably formed with wall 18 and are preferably joined at both ends. In this implementation the inner end of guide members 36 extends to second wall portion 32 and the outer end extends to flange 28. If desired the guide members 36 need not extend into either or both of the second wall portion 32 or the flange 28. In other words the guide members 36 may extend only within portion 34, only the portions 32 and 34, only the portions 28 and 34 or all three portions 28, 32 and 34 or the space portions defined by these wall portions or combinations of wall portions, i.e. space portion 35, space portions 33 and 35, space portions 35 and 39 or all three space portions 33, 35 & 39.

In this implementation each guide member 36 has an inner portion 38 and an outer portion 40. The inner portion 38 extends generally parallel/coaxially to the cannula 24 and is effectively an extension of the second wall portion 32 of tubular wall 18.

The outer portion 40 extends generally at the same angle as flange 28 to the longitudinal axis and can be considered to be an extension of the conical flange 28.

Referring to FIG. 5 it will be seen that a small diameter vial 50 inserted into the open end 20 of the sampling port, if inserted off centre, will have first contacted the outer portions 40 of guide members 36 and/or the flange 28. The outer portions 40 and flange 28 guide the vial 50 to be located centrally over cannula 24 and inner portions 38 prevent any significant sideways movement of the vial 50 as it is inserted further and impaled on the cannula.

FIG. 6 shows a slightly smaller vial 60 that has been inserted and impaled on cannula 24. There is a small gap 62 between the largest diameter portion of vial (the bung 64 in this case) and the guide members 36. However, this is relatively small and the guide members 36 have served to locate the vial 62 substantially coaxially with the cannula 24 and prevent significant tilting.

When a larger diameter vial 70 (see FIG. 7) is inserted into the sampling port it will first contact the outer portion of flange 28, which will guide the vial to be located centrally over cannula. Further inwards movement will result in the cap 72 of the vial 70 contacting outer portions 40 of guide members 36. The guide members are sufficiently flexible and deflect outwards as the vial 70 is pushed inwards, so allowing the larger diameter vial 70 to enter the larger diameter space portion 35. The larger diameter first space portion 35 is sized to accommodate the larger diameter vial 70 and so the vial may continue its inwards movement and be impaled on the cannula 24. The larger diameter first wall portion 34 will prevent any significant sideways movement of the vial as it is inserted further and impaled on the cannula.

The step 74 in the wall 18 between the first and second wall portions 32 and 34 acts to limit inwards movement of the vial 70. Inwards movement may also be limited by the rubber sheath 25.

Figure 1:
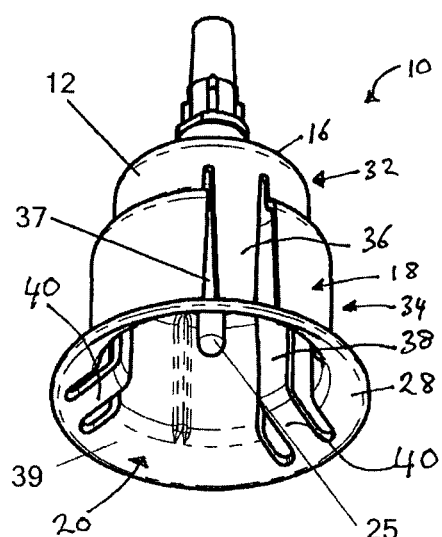
FIG. 1 is a perspective view from below of a sampling port according to a first implementation of the invention.
Figure 2:
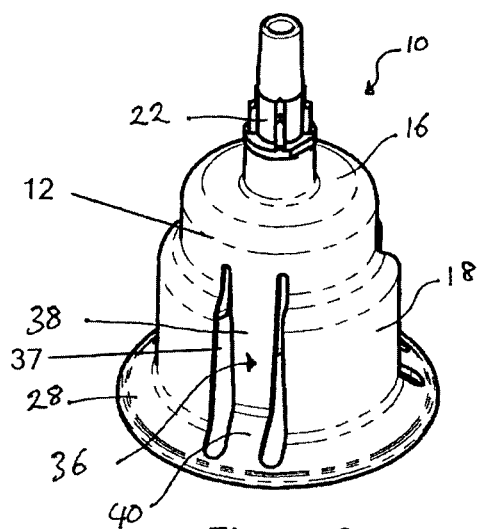
FIG. 2 is a perspective view from above of the sampling port of FIG. 1.

The deflection of guide members 36 is elastic and when the large diameter vial is removed the guide members 36 return elastically or spring back to the un-deflected state as shown in FIG. 1.

Figure 7:
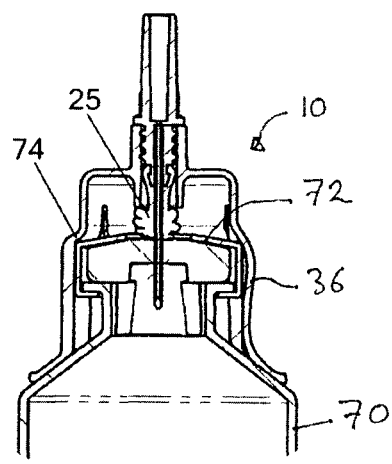
FIG. 7 is a cross sectional side view of the sampling port of FIG. 1 in use with a third size vial.
Figure 8:
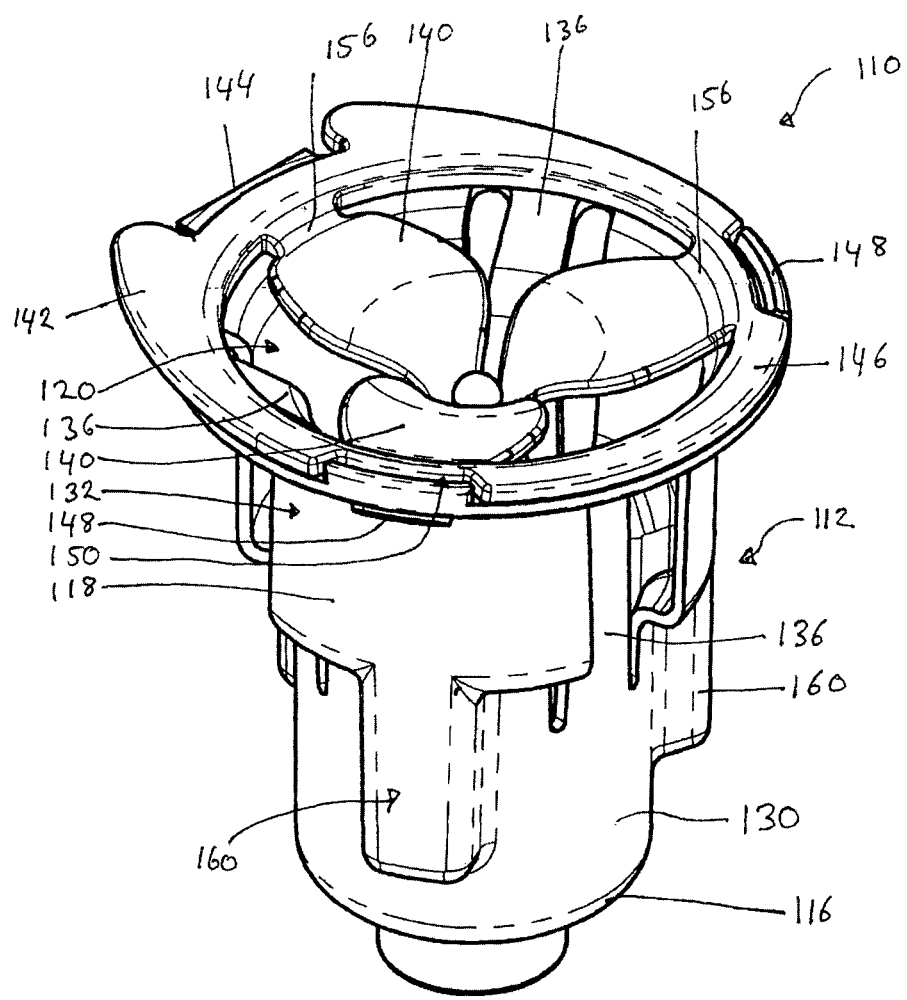
FIG. 8 is a perspective view of a sampling port according to a second implementation of the invention.
Figure 9:
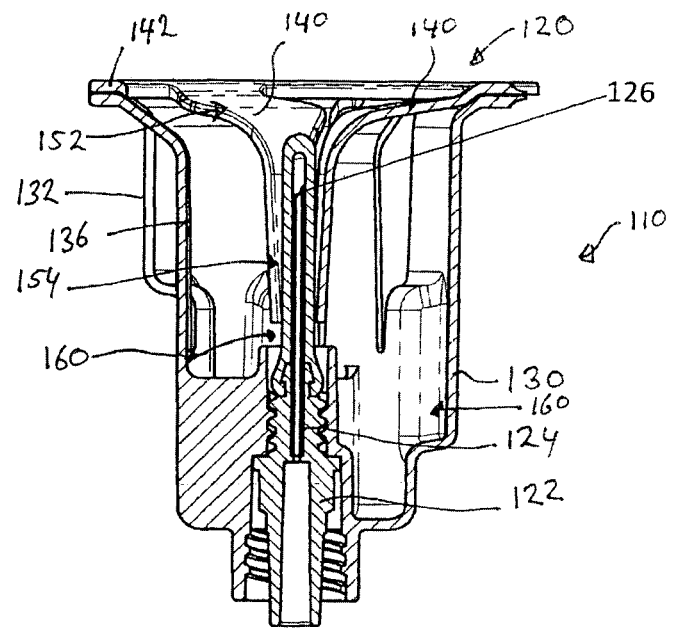
FIG. 9 is a first cross sectional side view of the sampling port of FIG. 8.
Figure 10:
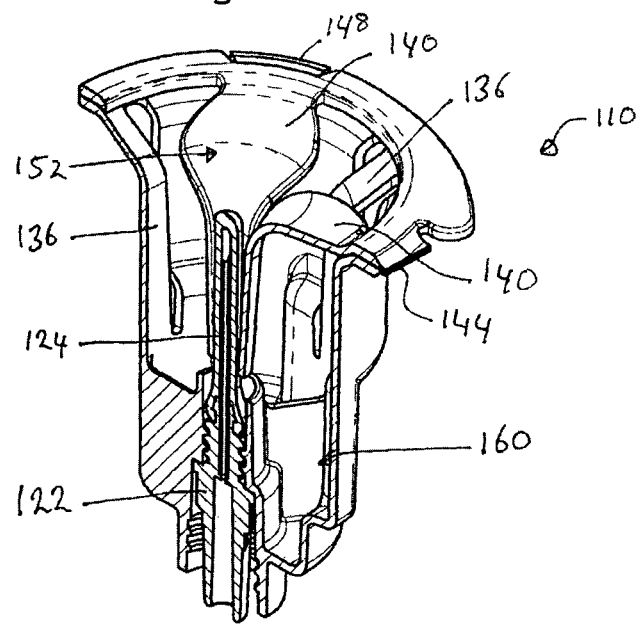
FIG. 10 is a cross sectional perspective view of the sampling port of FIG. 8.
Figure 11:
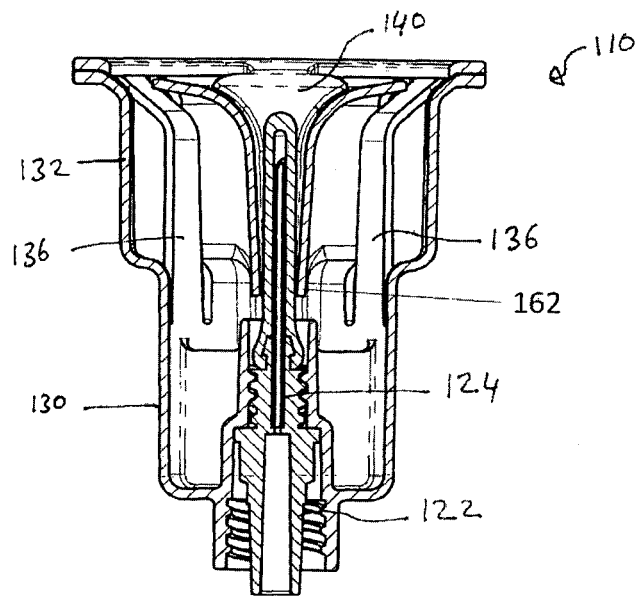
FIG. 11 is a second cross sectional side view of the sampling port of FIG. 8.
Figure 12:
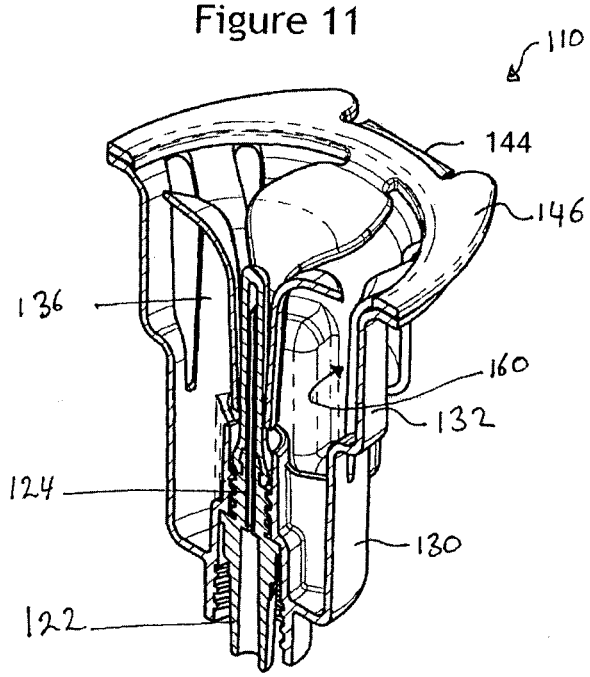
FIG. 12 is a second cross sectional perspective view of the sampling port of FIG. 8.

As seen in FIG. 7 the guide members 36 bend around the cap of the vial and do not have any definite or discrete hinge points. However, if desired a guide member 36 may have hinge points at one or more of its ends (where it connects to the inner wall portion 32 and flange 28) and/or the junction of portions 38 and 40.

Whilst is preferable that the guide members 36 be integrally formed with tubular wall 18, this is not essential and a separate component may be provided that is mounted on the sampling port body 12.

Whilst is preferable that the guide members 36 are joined at both ends to wall 18 this is not essential and the guide members 36, if formed with wall 18, may be joined at only one end.

Whilst is preferable that the guide members 36 extend into and from the flange area this is not essential and if desired the guide members 36 could extend inwards from the wall portion 34. If desired the guide members 36 could extend from the wall portion 32 into the first space portion 35, with the guide members 36 spaced from the wall portion 34. The slots 37 may remain, to receive the deflected guide members 36.

FIGS. 8 to 12 show a sampling port 110 according to another implementation of the invention.

The sampling port is similar to sampling port 10 and has a generally tubular guard body 112 similar to the body 12 of sampling port 10. Body 112 has a base 116 at one end and a tubular side wall 118 that extends away from the base 116. The tubular side wall 118 defines an open end 120. Mounted on the base 116 is needle assembly 122 with cannula 124. The cannula 124 is mounted generally centrally and extends along the body toward the open end 120. The free end 126 of the cannula 124 is preferably spaced from the open end 120. A conical flange 128 extends from the open end 120 of the side wall 118.

The tubular side wall 118 has second wall portion 130 of one diameter near the base 116 and first wall portion 132 of a larger diameter further away from the base 16. Three guide members 136 extend inwards from the larger diameter first wall portion 132. The guide members function substantially the same as described with reference to the first implementation shown in FIGS. 1 to 7.

Three protective members 140 extend inwards from adjacent the opening 120 toward the cannula. Each protective member 140 is located between guide members 136 and extends inwards toward the axis of the port and then downwards adjacent the cannula 124.

In this implementation the protective members 140 are part of a cap 142 formed with body 112. Cap is hinged to body 112 at hinge area 144 and comprises a ring 146 from which the protective members 140 extend. The ring 146 extends over the free end of flange 122 and has barbed legs 148 that pass through openings 150. If desired the cap 142 may be formed as a separate component and attached to the body 112 using barbed legs 148 or other means. A third barbed leg 148 may be used where hinge 144 is located.

The protective members 140 have a first portion 152 that extends radially inwards and at a relatively shallow angle to the axis of the body 112 and substantially block access to the cannula 126. A second portion 154 extends generally axially toward base 116 and alongside cannula 124. The space between cannula 124 and portions 154 is less than the diameter of a small sampling vial and, more importantly, smaller than the size of a finger of most users. The radially inwards directed first portion 152 thus serves to substantially prevent accidental contact with cannula 124 by a finger or other body part.

In use, insertion of a vial into the open end 120 of sampling port 110 causes the end of the vial to contact protective members 140. The force applied causes the protective members to bend and/or rotate about respective hinge 156, formed at the junction of each protective member 140 with ring 146.

This bending and/or rotation causes the axially extending second portions 154 to move away from the cannula, so allowing the vial to be inserted into the body 12 and impaled on the cannula.

When a small diameter vial is inserted that has a diameter the same or less than the diameter defined by guide members 136, only the protective members 150 are deflected. The vial is then guided by guide members 136 onto the cannula 124.

When a large diameter sampling vial is inserted both the protective members 140 and the guide members 136 are deflected outwards. Some vials have a cap or head that is larger another part the vial, such as the neck. The second portion 154 of protective members 140 extends sufficiently toward base 116 so that they contact the sides of the cap when the vial is fully inserted into the sampling port. If the cap fully passes the portions 154 they would move radially inward to be against the smaller diameter portion and so prevent removal of the vial.

The protective members 140 are an additional component and so when a large diameter vial is inserted the protective members are located between the vial and the larger diameter portion 132 of body 112. Accordingly, the portion 132 needs to be configured so that the effective diameter is large enough for the vial. This may be by increasing the diameter overall of portion 132, as in this implementation, or by providing recesses into which the protective members may be received. In this implementation a large diameter vial thus contacts and is guided by the protective members 140 and guide members 136 and does not contact the side wall itself.

The protective members 140 extend into the small diameter second space portion 130 and in this implementation the small diameter second space portion 130 is provided with recesses 160 to receive the free end portions 162 of the protective members. These recesses extend near to base 16 to accommodate the increased axial length of the protective members 140 due to the straightening affect as they are deflected and/or bent by the vial.

If desired the protective members 140 may be made with no inner portions whatsoever or inner portions that do not extend as far toward base 116. If sufficiently short the need for recesses 160 or the like may be avoided.

As with the first implementation the guide members 136 do not need to extend from the open end of the body 112 through all three space portions and, so long as at least part of a guide member is in the first space portion defined by wall portion 132 a guide member may extend into either or both of the other space portions or the wall portions defining these space portions.

Figure 13:
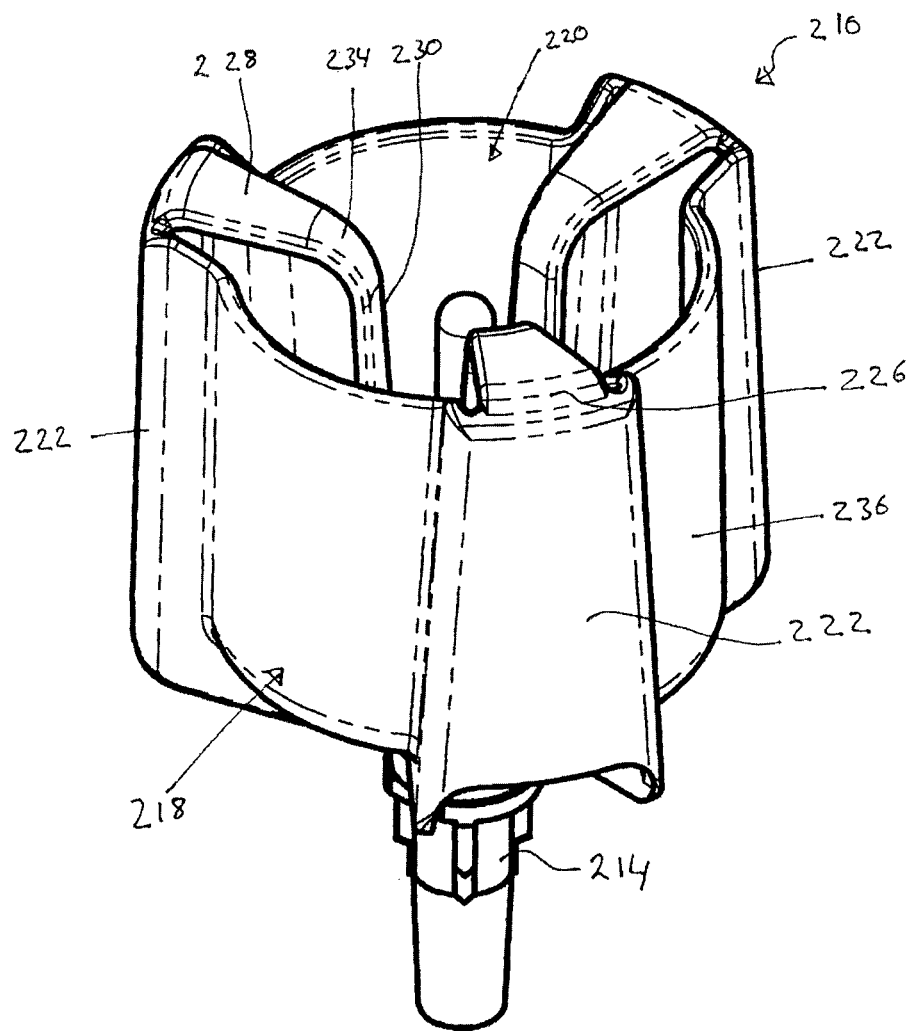
FIG. 13 is a perspective view of a sampling port according to a third implementation of the invention.
Figure 14:
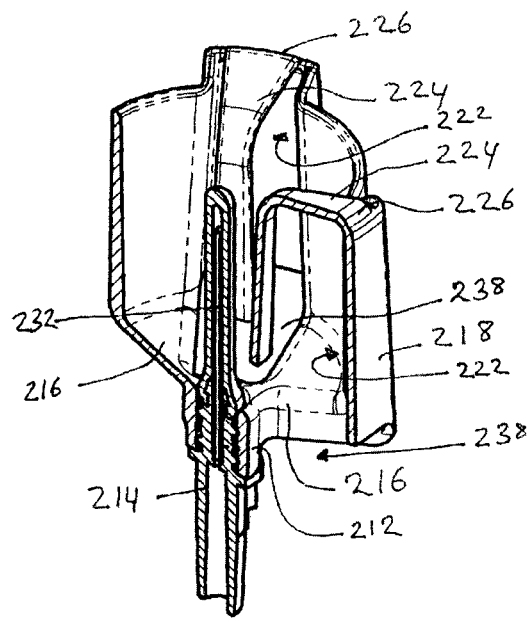
FIG. 14 is a first cross sectional perspective view of the sampling port of FIG. 13.
Figure 15:
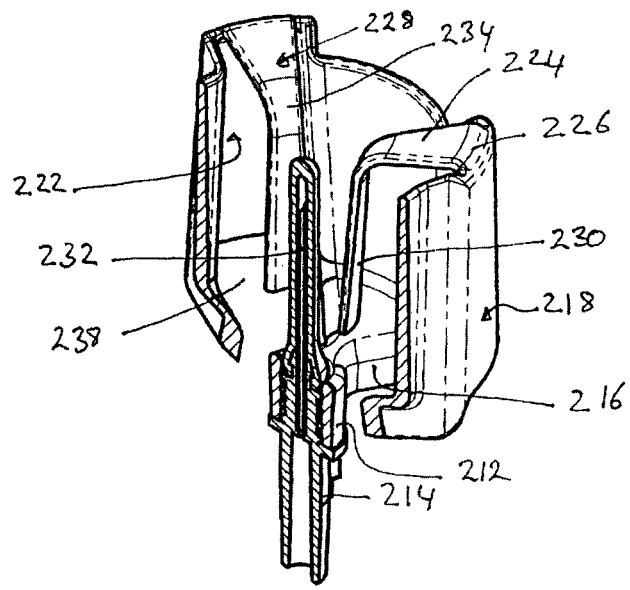
FIG. 15 is a second cross sectional perspective view of the sampling port of FIG. 13.
Figure 16:
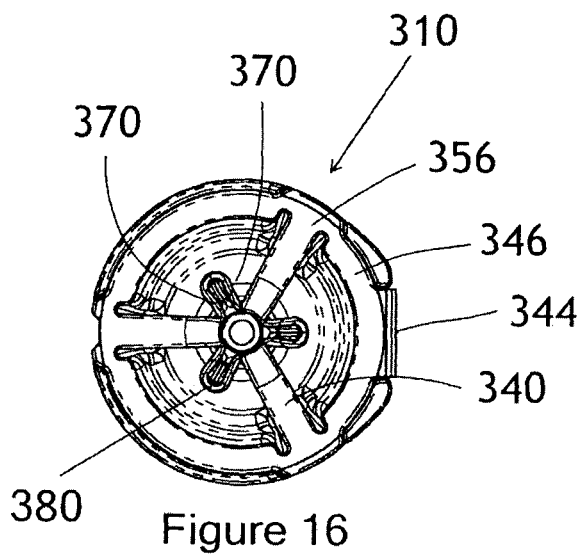
FIG. 16 is a plan view from above of a sampling port according to a fourth implementation of the invention.
Figure 17:
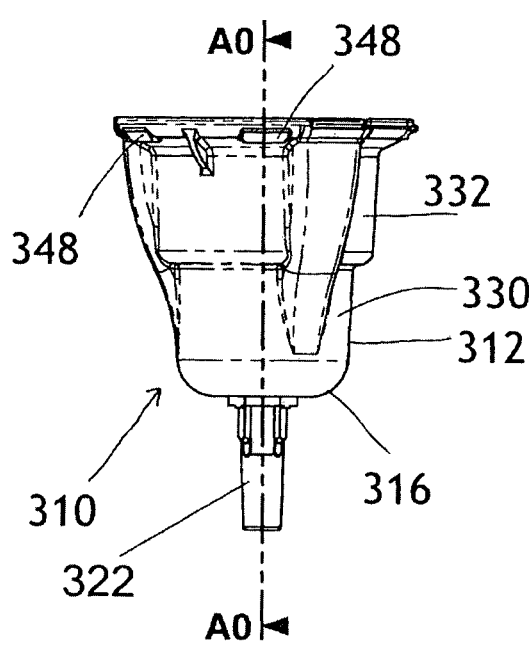
FIG. 17 is a side view of the device of FIG. 16.
Figure 18:
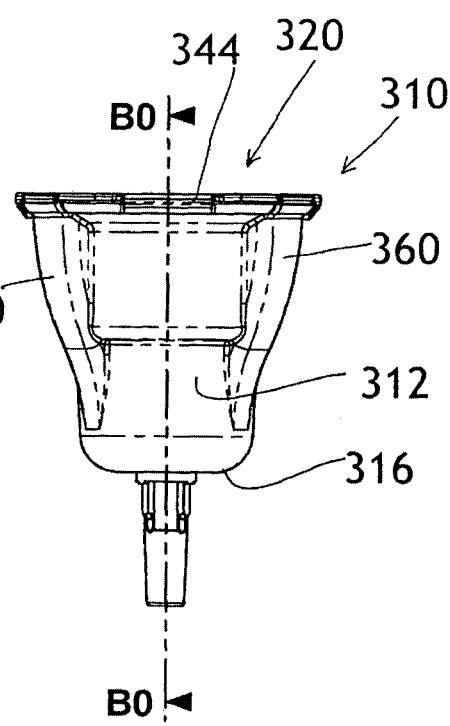
FIG. 18 is another side view of the device of FIG. 16.
Figure 19:
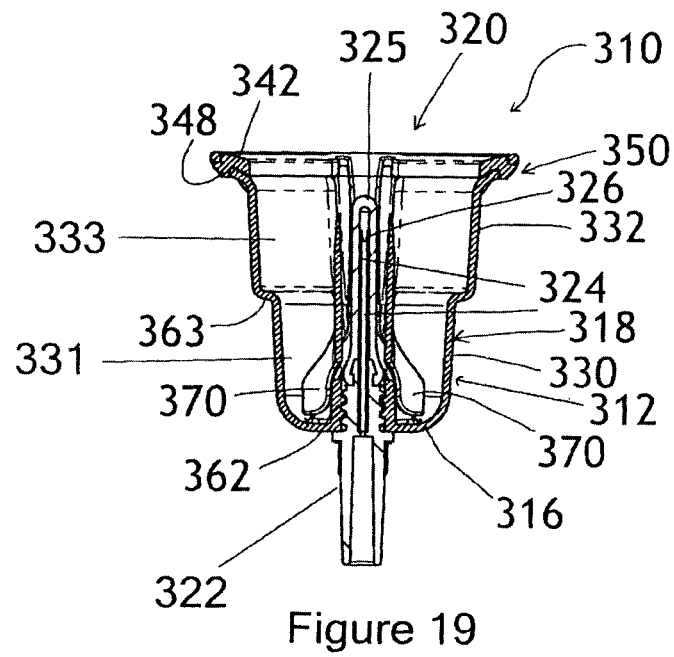
FIG. 19 is a cross sectional side view of the sampling port taken along line AO-AO of FIG. 17.
Figure 20:
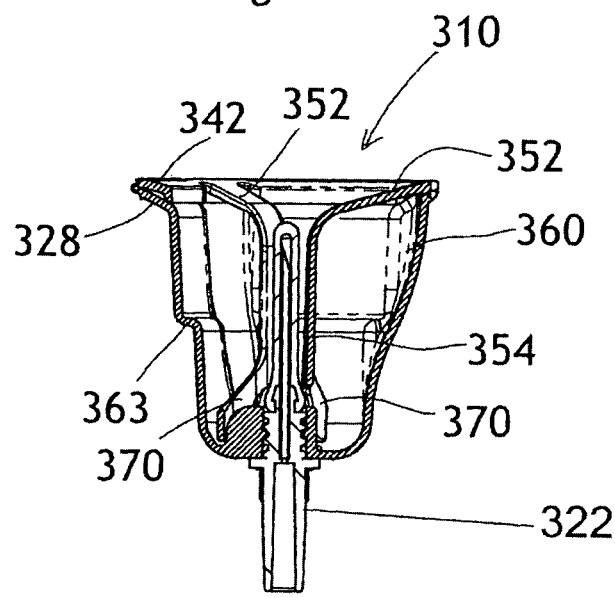
FIG. 20 is a second cross sectional side view of the sampling port taken along line BO-BO of FIG. 18.

FIGS. 13 to 15 show a sampling port 210 according to a third implementation of the invention.

The sampling port 210 has a hub 212 in which needle assembly 214 is mounted. Rather than a solid base, three arms 216 extend radially outwards from hub 212.

Wall 218 extends upwards from arms 216 and defines a generally cylindrical space 220 with three recesses 222 spaced about the circumference.

Three guide members 224 extend from the wall 218 and are each rotatable about area hinge 226. Each guide member 224 has a first portion 228 that extends generally radially and slightly downwards toward cannula 232 and a second portion 230 that extends generally alongside to cannula 232 toward arms 216.

In use a vial with a diameter the same or smaller than the effective diameter of the three guide members 224 is inserted into the space so defined and guided by the guide member onto cannula 232 without significant deflection of guide members 224.

When larger size vials are inserted the guide members 224 rotate and/or flex to increase the effective size of the opening to allow the larger size vial to be inserted into the sampling port and guided onto the cannula. To accommodate larger vials the guide members may flex about the junction 234 of the first and second portions 228 & 230.

The recesses 222 allow the guide members to be rotated and/or deflected fully out of the notional cylinder defined by cylindrical portions 236 of wall 218. The gaps 238 between arms 216 are provided as the guide members effectively lengthen extend though the openings when large diameter vials are inserted.

FIGS. 16 to 22 show a sampling port 310 according to a fourth embodiment of the invention.

The sampling port 310 has a generally tubular guard body 312. Body 312 has a base 316 at one end and a tubular side wall 318 that extends away from the base 316 to define a space having a longitudinal direction. The tubular side wall 318 defines an open end 320. Mounted on the base 316 is needle assembly 322 with cannula 324. The cannula 324 is mounted generally centrally and extends along the body toward the open end 320. The free end 326 of the cannula 324 ends short of the open end 320.

The tubular side wall 318 has second wall portion 330 of one size near the base 316 and first portion 332 of a larger size further away from the base 316. These first and second wall portions are generally circular in cross section but have recesses 360. First and second wall portions 332 and 330 define first and second space portions 333 and 331 respectively In this implementation, three guide (and protective) members 340 extend inwards from adjacent the opening 320 toward the cannula 324. Each guide member 340 extends inwards toward the axis of the port and then downwards adjacent the cannula 324. There could be more or fewer than three guide members.

In this implementation the guide members 340 are part of a cap 342 formed with body 312. Cap is hinged to body 312 at hinge area 344 and comprises a ring 346 from which the guide members 340 extend. The ring 346 extends over the free end of flange 328 and has barbed legs 348 that pass through openings 350. If desired the cap 342 may be formed as a separate component and attached to the body 312 using barbed legs 348 or other means. A third barbed leg 348 may be used where hinge 344 is located.

The guide members 340 have a first portion 352 that extends radially inwards and at a relatively shallow angle to the axis of the body 312 and substantially block access to the cannula 324. A second portion 354 extends generally axially toward base 316 and alongside cannula 324. The space between cannula 324 and portions 354 is less than the diameter of a small sampling vial and, more importantly, smaller than the size of a finger of most users. The radially inwards directed portion 352 thus serves to substantially prevent accidental contact with cannula 324 by a finger or other body part.

The ends of each of the three guide members 340 split near the base 316 into two arms 370. Each arm 370 is joined to the adjacent arms 370 of the other two arms. Arms 370 are joined or formed together at 380.

In use, insertion of a vial into the open end 320 of sampling port 310 causes the end of the vial to contact guide members 340. The force applied causes the guide members to bend and/or rotate about respective hinge area 356, formed around the junction of each guide member 340 with ring 346.

This bending and/or rotation causes the axially extending portions 354 to move away from the cannula, so allowing the vial to be inserted into the body 312 and impaled on the cannula 324 whilst being guided by guide members 340 or wall 318 or both guide members 340 and wall 318. The lower portions 354 are also caused to bend or deflect about the junction with portions 352 and generally straighten.

When a vial with a large diameter is inserted, the guide members are located between the vial and the larger diameter first space portion 332 of body 312. Accordingly, the portion 332 needs to be configured so that the effective diameter is large enough for the vial. This may be by providing recesses 360 into which the guide members may be received, as in this implementation, or by increasing the diameter overall of portion 332.

Figures 21, 22:
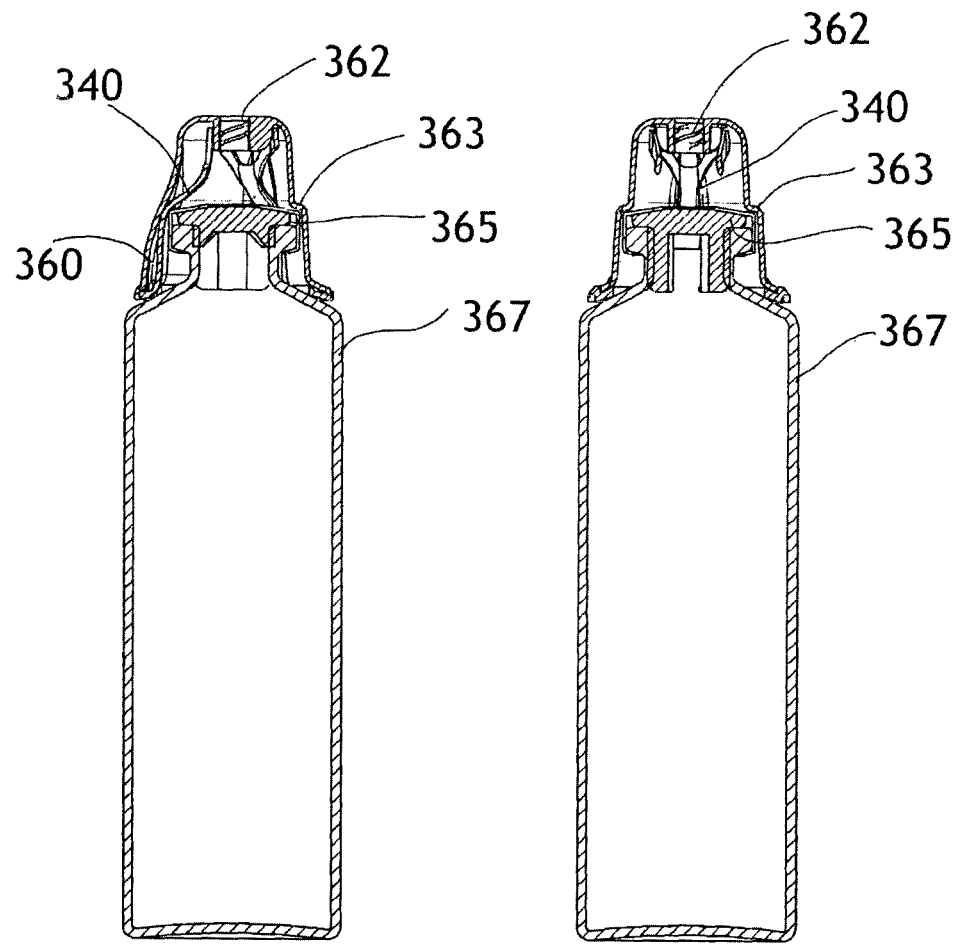
FIG. 21 is a cross sectional side view showing a vial inserted into the sampling port of FIG. 16, taken along a line corresponding to line BO-BO of FIG. 18 and in which the needle assembly is omitted for clarity.
FIG. 22 is a cross sectional side view showing a vial inserted into the sampling port of FIG. 16, taken along a line corresponding to line AO-AO of FIG. 17 and in which the needle assembly is omitted for clarity.
Figure 23:
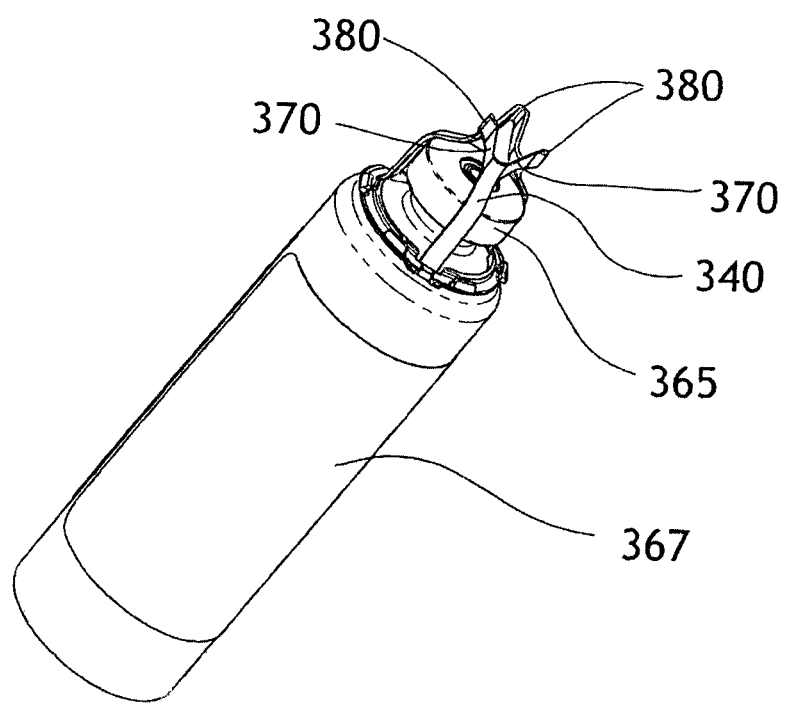
FIG. 23 is a perspective view showing a vial inserted into the sampling port of FIG. 16 and in which the outer body has been omitted for clarity.

In this implementation a large diameter vial having a size the same or slightly smaller than the diameter of the larger first space portion 332 thus contacts and is guided by the side wall itself. Insertion into the port is limited by the step 363 between the larger first space portion 332 and the smaller second space portion 330. As seen in FIG. 21 the guide members 340 move into the recesses 360.

When a "large" vial having a diameter smaller than the large first space portion 333 but larger than the small space portion 331 is used it contacts and is guided by the guide members 340 and does not contact the side wall itself. Again insertion into the port is limited by the step between the smaller and larger sized space portions 330 and 332.

The recesses 160 extend into the smaller diameter second space portion 330 to allow a guide member to bend around the vial, again as seen in FIG. 21.

A "small" vial having a diameter smaller than the diameter of the smaller second space portion 331 contacts and is guided by the guide members 340 into the second space portion 330 and does not contact the side wall 318 itself.

Some vials have a cap or head that is larger another part the vial, such as the neck. If the cap fully passes the portions 354 the portions 354 would move radially inward to be against the smaller diameter portion and so prevent removal of the vial. The arms 370 and joining portion 380 prevent this. Insertion into the port is limited by the needle assembly or by the arms 370. The arms 370 are sufficiently loose about the mounting for the needle assembly that the ends of the guide members may move axially as they are deflected radially as a vial is inserted into the port. The body may also be provided with corresponding surface(s) that limit outwards movement of the guide members.

In this implementation, although the recesses 360 extend into the smaller second space portion 330 during use with a smaller vial, the guide members 340 are generally located between the wall 318 and the vial.

As can be seen in FIGS. 19 to 22, the arms 340 extend past the mounting 362 for the needle assembly. Accordingly, if desired, joining of the guide members 340 by the arms 370 may be omitted. In such a configuration the smaller second space portion 331 may be made smaller to guide a small vial, with larger recesses provided for the guide members 340, in a similar manner to the embodiment of FIGS. 8 to 12.

In this embodiment the three guide members 340 are integral with the ring 346 and connected to each other adjacent base 316. An alternate configuration is that the guide members 340 are mounted to the cup 312 rather than each other so as to limit sideways movement near the base. If mounted to the cup 312 this may be by way of a portion of each guide member 340 retained in but sliding in an axial slot, so as to allow axial movement.

As with the first and second implementations the guide members 340 do not need to extend from the open end of the body 312 through all three space portions and, so long as at least part of a guide member is in the first space portion defined by wall portion 332 a guide member may extend into either or both of the other space portions or the wall portions defining these space portions.

Unless the context clearly requires otherwise, throughout the description and any claims the words "comprise", "comprising", and the like are to be construed in an inclusive sense as opposed to an exclusive or exhaustive sense; that is to say, in the sense of "including, but not limited to".

The features of the invention described or mentioned in this document may be combined in any combination of features where features are not mutually exclusive.

It will be apparent to those skilled in the art that many obvious modifications and variations may be made to the embodiments described herein without departing from the spirit or scope of the invention.

The claims defining the invention are as follows:

1. A sampling port having:
   a body having a longitudinal direction and adapted to receive a sampling vial, the body comprising:
      at least one first wall portion defining a tubular first space portion adapted to receive a vial having a first diameter and having an open end;
      at least one flange member extending radially inwards from the at least one first wall portion
      at least one second wall portion depending from the at least one flange member and extending away from the open end;
      the at least one second wall portion having first and second ends with the first end spaced from the open end and nearer the open end than the second end and;
   at least one guide member extending longitudinally past the first end toward the open end into the first space portion and past the first end toward the second end;
   a tubular second space portion coaxial with the first space portion defined by at least one of the at least one second wall portion and the at least one guide member, the second space portion adapted to receive a vial having a second diameter, smaller than the first diameter;
   a cannula having a longitudinal axis and extending longitudinally within the first and second space portions with a pointed end located within the first space portion and nearer the open end than the first end and facing the open end, whereby a vial passed into the body from the open end may be impaled on the cannula;
   the at least one guide member extending longitudinally alongside the pointed end;
   the at least one guide member defining at least in part a third tubular space portion, located at least partially within the first space portion, the third tubular space portion having a third diameter less than the first diameter;
   the at least one guide member engaging and guiding said vial of the second diameter when in the first space portion onto the cannula and into the second space portion when inserted into the open end;
   the at least one guide member movable to allow a vial of a size larger than the second diameter to be inserted into the body and to be engaged and guided by the at least one guide member and/or the at least one first wall portion onto the cannula.

2. The sampling port of claim 1 wherein the at least one guide member is formed with at least one of the at least one first and second wall portions.

3. The sampling port of claim 2 wherein at least one of the at least one first and second wall portions has at least one guide member recess adapted to receive at least part of a guide member.

4. The sampling port of claim 3 wherein the at least one guide member recess comprises at least one slot in at least one of the at least one first and second wall portions.

5. The sampling port of claim 3 wherein the at least one guide member recess is sized so said at least part of a guide member is located equidistant with an adjacent wall portion from the axis of the cannula or further from the axis of the cannula than an adjacent wall portion.

6. The sampling port of claim 4 wherein, when deflected, at least a portion of said at least part of a guide member extends through the at least one slot.

7. The sampling port of claim 3 wherein the at least one guide member has a first guide portion that extends parallel to the longitudinal axis.

8. The sampling port of claim 7 wherein the first guide portion and at least part of the at least one second wall portion are located the same distance from the longitudinal axis.

9. The sampling port of claim 8 wherein the at least one guide member is connected to the at least one second wall portion intermediate the first and second ends.

10. The sampling port of claim 9 wherein the at least one guide member is at least partially defined by two spaced apart slots in at least one of the at least one first and second wall portions.

11. The sampling port of claim 10 wherein the at least one guide member comprises at least one vial centering portion that extends from the at least one first guide portion toward the at least one first wall portion.

12. The sampling port of claim 6 wherein the at least one guide member is connected to at least one of the at least one first and second wall portions for movement about at least one hinge axis extending in a plane generally orthogonal to the longitudinal axis.

13. The sampling port of claim 10 wherein the third diameter is the same as the second diameter.

14. The sampling port of claim 1 wherein the third diameter is less than the second diameter.

15. The sampling port of claim 14 wherein the at least one guide member extends within the second space portion.

16. A sampling port having:
   a body having a longitudinal direction and adapted to receive a sampling vial, the body comprising
      at least one first wall portion defining a tubular first space portion adapted to receive a vial having a first diameter and having an open end;
      at least one flange member extending radially inwards from the at least one first wall portion
      at least one second wall portion depending from the at least one flange member and extending away from the open end;
      the at least one second wall portion having first and second ends with the first end spaced from the open end and nearer the open end than the second end and;
   at least one guide member extending longitudinally past the first end toward the open end into the first space portion and past the first end toward the second end;
   a tubular second space portion coaxial with the first space portion defined by the at least one second wall portion and the at least one guide member, the second space portion adapted to receive a vial having a second diameter, smaller than the first diameter;
   a cannula having a longitudinal axis and extending longitudinally within the first and second space portions with a pointed end located within the first space portion and nearer the open end than the first end and facing the open end, whereby a vial passed into the body from the open end may be impaled on the cannula;
   the at least one guide member extending longitudinally alongside the pointed end;
   the at least one guide member defining at least in part a third tubular space portion, located at least partially within the first space portion, the third tubular space portion having a third diameter less than the first diameter;

the at least one guide member engaging and guiding said vial of the second diameter when in the first space portion onto the cannula and into the second space portion when inserted into the open end;

the at least one guide member movable to allow a vial of a size larger than the second diameter to be inserted into the body and to be engaged and guided by the at least one guide member and/or the at least one first wall portion onto the cannula, wherein the at least one guide member comprises at least one first guide portion connected to the at least one second wall portion intermediate the first and second ends;

the at least one first guide portion and the at least one second wall portion extend substantially parallel to the longitudinal axis;

the at least one guide member having at least one vial centering portion that extends from the at least one first guide portion toward the at least one first wall portion;

the at least one first wall portion and at least one second wall portion including at least one slot therein aligned with the at least one guide member whereby when deflected at least a part of the at least one guide member extends into or through the at least one slot.

17. A sampling port having:

a body having a longitudinal direction and adapted to receive a sampling vial, the body comprising
- at least one first wall portion defining a tubular first space portion adapted to receive a vial having a first diameter and having an open end;
- at least one flange member extending radially inwards from the at least one first wall portion
- at least one second wall portion depending from the at least one flange member and extending away from the open end;
- the at least one second wall portion having first and second ends with the first end spaced from the open end and nearer the open end than the second end and;
- at least one guide member extending longitudinally past the first end toward the open end into the first space portion and past the first end toward the second end;

a tubular second space portion coaxial with the first space portion defined by the at least one second wall portion and the at least one guide member, the second space portion adapted to receive a vial having a second diameter, smaller than the first diameter;

a cannula having a longitudinal axis and extending longitudinally within the first and second space portions with a pointed end located within the first space portion and nearer the open end than the first end and facing the open end, whereby a vial passed into the body from the open end may be impaled on the cannula;

the at least one guide member extending longitudinally alongside the pointed end;

the at least one guide member engaging and guiding said vial of the second diameter when in the first space portion onto the cannula and into the second space portion when inserted into the open end;

the at least one guide member movable to allow a vial of a size larger than the second diameter to be inserted into the body and to be engaged and guided by the at least one guide member and/or the at least one first wall portion onto the cannula, wherein the at least one guide member comprises at least one first guide portion located nearer the cannula than the at least one second wall portion intermediate the first and second ends;

the at least one guide member having at least one vial centering portion that extends from the at least one first guide portion toward the at least one first wall portion;

the at least one guide member defining at least in part a third tubular space portion, located at least partially within the first space portion, the third tubular space portion having a third diameter less than the first and second diameters;

the at least one first wall portion and at least one second wall portion including at least one slot or recess therein aligned with the at least one guide member whereby when deflected at least a part of the at least one guide member extends into or through the at least one or recess.

* * * * *